United States Patent [19]

Young

[11] 4,018,769

[45] Apr. 19, 1977

[54] UREA CYANURATE MANUFACTURE
[75] Inventor: Donald C. Young, Fullerton, Calif.
[73] Assignee: Union Oil Company of California, Brea, Calif.
[22] Filed: May 17, 1976
[21] Appl. No.: 687,363
[52] U.S. Cl. .................................. 260/248 NS
[51] Int. Cl.² .................................. C07D 251/30
[58] Field of Search ...... 260/248 A, 248 NS, 249.5
[56] References Cited
UNITED STATES PATENTS 3,154,545  10/1964  Symes et al. ............... 260/249.5 X Primary Examiner—John M. Ford
Attorney, Agent, or Firm—Richard C. Hartman; Dean Sandford

[57] ABSTRACT

Urea cyanurate is obtained by heating urea to temperatures above 190° C. in the presence of catalytic amounts of elemental sulfur. Cyanuric acid is obtained by hydrolysis or pyrolysis of the urea cyanurate product.

8 Claims, No Drawings

UREA CYANURATE MANUFACTURE

BACKGROUND OF THE INVENTION

The manufacture of urea cyanurate and cyanuric acid are reported in the literature. Beilstein, Volume 26, original edition, reports the manufacture of urea cyanurate by adding cyanuric acid to supersaturated aqueous urea at elevated temperatures. Symes and Vazopolos report in U.S. Pat. No. 3,154,545 that urea cyanurate can be obtained by contacting urea and cyanuric acid at temperatures between 180° and 320° C. Both procedures require cyanuric acid as starting material. Cyanuric acid can be obtained in relatively pure form from urea cyanurate.

However, it is more difficult to obtain cyanuric acid directly from urea. For instance, cyanuric acid can be obtained by pyrolyzing urea at atmospheric pressure and temperatures of 180° C. or more. However, this reaction is highly inefficient and results in substantial reactant loss and byproduct formation. At these temperatures, unless it is rapidly converted to a stable product, urea will volatilize and isomerize to numerous byproducts including ammonium cyanate, ammeline, melamine, biuret, triuret, dicyandiamide, ammelide, cyanic acid, and/or ammonium carbonate. It may also pyrolyze to ammonia, carbon dioxide and water. These side reactions are significant. They promote considerable reactant loss and product contamination with impurities which can be separated from cyanuric acid only with considerable difficulty.

It has been suggested that these shortcomings can be overcome, at least to a degree, with catalysts such as ammonium chloride or a zinc chloride. Such procedures are described in the Journal of the Society of Chemical Industry, Volume 67 (1948) and U.S. Pat. No. 2,527,316. While these catalysts may reduce some of the side reactions referred to above, they do not eliminate those reactions. As reported by Symes et al, supra, the yields are generally 60 percent cyanuric acid or less and the products contain substantial amounts of impurities such as ammelide and the like.

Moreover, these investigators do not report any yields of urea cyanurate. Thus, even if their methods could convert urea directly to cyanuric acid, it would still remain for the practitioner to separate the cyanuric acid from interfering byproducts and then convert it to urea cyanurate by reaction with urea under conditions such as those described above.

It is therefore one object of this invention to provide an improved method of producing urea cyanurate. Another object is the provision of a method of producing urea cyanurate directly from urea in high yields and in the substantial absence of byproducts. Another object is the provision of a method for obtaining substantially pure cyanuric acid from urea.

In accordance with one embodiment, urea cyanurate is obtained directly from urea by contacting substantially undissolved urea with a catalytic amount of elemental sulfur under substantially anhydrous conditions at a temperature of about 190° to about 320° C. for a period of time sufficient to convert at least a portion of the urea to a reaction product containing urea cyanurate. The presence of urea cyanurate can be readily detected by the analytical procedures described hereinafter including ultraviolet, spectroscopy, mass spectroscopy, thin layer chromatography and/or elemental analysis. The presence of water insoluble compounds, i.e., urea cyanurate, can be readily determined by mixing the reaction product with sufficient water to dissolve any unreacted urea. An insoluble solid phase will remain undissolved under mild conditions. High temperatures and long contact times, however will hydrolyze the urea cyanurate to urea and cyanuric acid or decomposition products thereof, all of which are water soluble. Such conditions should be avoided for the purposes of detecting urea cyanurate.

Relatively low reaction temperatures within the described range are preferred due to the fact that byproduct formation accelerates at higher temperature. Urea pyrolysis and loss as ammonia, CO and $Co_2$ also increase at higher temperatures. Thus, in most instances, it is preferable to operate at temperatures within a range of about 190° to about 260° C. Under these conditions both the urea and elemental sulfur are present as two separate molten phases. Thus, mechanical or fluidizing agitation means should be provided to assure intermixing.

Substantial conversions require contact times of at least 1 minute, generally between about 1 minute and about 1 hour, preferably between about 2 and about 10 minutes. However, reaction rate accelerates at elevated temperatures. So does the byproduct formation and urea pyrolysis. Thus reaction temperature and time should be correlated to obtain acceptable conversion levels in a single pass while minimizing byproduct make and urea pyrolysis. In other words, lower reaction temperatures are employed at higher contact times. Conversely, reaction times of less than 30 minutes, preferably less than 15 minutes, are used at the higher reaction temperatures, e.g., 230° C. and above.

Sulfur does not participate in the reaction and does not combine with the reactants, products or byproducts. Thus it can be recovered from the reaction product and recycled. The sulfur is used in catalytic amounts sufficient to promote the reaction. These amounts can be readily determined by combining urea and sulfur in different proportions, contacting the two materials at a series of different temperatures, e.g., 200°, 220°, 260° and 280° C., each at several different contact times, to ascertain which combination of conditions is best suited for a given installation. For instance, some users may prefer higher sulfur concentrations and lower reaction temperatures and longer contact times to obtain substantial conversions in a single pass while minimizing byproduct formation and pyrolysis. Conversely, the contact time required to obtain a given conversion in a single pass can be decreased by increasing sulfur concentration and/or reaction temperature when somewhat higher byproduct yields can be tolerated. As a general rule, however, sulfur content will correspond to a least about 1, usually between 1 and about 100 weight parts elemental sulfur per weight part urea.

Substantially anhydrous conditions are also preferred at reaction temperature. Thus the system should contain less than 5 weight parts water per weight part urea at 190° C. or above. In addition to dissolving the urea reactant, water also accelerates hydrolysis of both urea and urea cyanurate. While other solvents for urea can be employed, they are not presently preferred for several reasons. Solvents complicate the separation of urea cyanurate from unreacted urea. They also appear to contribute to the formation of byproducts such as ammelide and melamine, urea pyrolysis and/oor hydrolysis, and urea cyanurate hydrolysis to cyanuric acid and urea.

The reaction product should be cooled before contacting a substantial amount of water to optimize urea cyanurate recovery. Although significant recovery can be obtained by rapid or even gradual quenching from reaction temperature with water, I prefer to first reduce the temperature to 110° C. or even 90° C. or less. The combination of water and elevated temperature accelerates hydrolysis to cyanuric acid which may not be desired. However, water can be added prior to cooling if the cyanuric acid is desired.

After cooling, the product can be contacted with sufficient water to form liquid and solid phases. The liquid phase contains water soluble reactants and by-products such as urea, while the solids phase contains urea cyanurate which can be recovered by separation from the supernatant aqueous phase. The amount of water required to accomplish this result will usually be at least about 10 weight parts water per 100 weight parts total product. Substantially higher water concentrations can be employed. However, extended contact, even at relatively low temperatures, should be avoided to minimize urea cyanurate hydrolysis. The rate of hydrolysis is reduced as temperature is reduced. Thus it is presently preferred that water washing be performed at temperatures below 40° C., conveniently between about 0° and about 40° C.

Additionally, the total washing volume is preferably minimized or limited to that required to accomplish the desired separation of urea from the reaction product. Urea is very soluble in water and substantially all of the unreacted urea can be recovered with relatively minor volumes. Limiting wash volume facilitates recovery of urea from solution and recycling it, either with or without wash water, to a urea manufacturing plant where it can be dehydrated and recovered in substantially pure form. In the alternative, urea can be recovered by evaporation, and can then be recycled as reactant.

The urea cyanurate product is a finely divided, friable powder as formed. It can be separated from the elemental sulfur by any one of several procedures. For example, the combination can be agitated in sufficient cold water to form a suspension of the urea cyanurate powder. The elemental sulfur, being more dense, will remain preferentially at the bottom of the container. Thus the two can be separated by decanting the suspension and filtering to recovery urea cyanurate. Trace sulfur carried over with the product can be removed by washing with carbon bisulfide or other material which is a preferential solvent for sulfur. These solvents should have an affinity for sulfur at least 5 times greater than their affinity for urea cyanurate. Illustrative solvents include benzene, toluene, xylene, acetone, ammonia, amyl alcohol, aniline, dichlorethylene, hexane, phenol, pyridine and quinoline.

In another embodiment, relatively pure cyanuric acid is obtained in high yields from urea by converting the urea to urea cyanurate as described above and hydrolyzing to obtain cyanuric acid and urea. The urea cyanurate can be hydrolyzed by contacting with at least about 1 mole of water per mole of urea cyanurate. About 1 to about 5 molar excess of water based on urea cyanurate can be employed. The water content is preferably minimized to obtain relatively concentrated urea solutions. Concentrated solutions facilitate handling and separation of cyanuric acid and urea upon cooling as described hereinafter.

Hydrolysis rate is accelerated by acidic conditions. Thus the urea cyanurate is preferably hydrolyzed in the presence of minor amounts of mineral acids such as hydrochloric, sulfuric, phosphoric, nitric and the like. Acid concentration should be sufficient to obtain a pH of about 6 or less although pH levels substantially below 1 should be avoided.

Hydrolysis rate also increases with temperature. However, urea hydrolysis also becomes significant at temperatures above 80° C. Thus, while temperatures of at least about 50° C. are effective, temperatures within the range of about 50° to about 150° C. are preferred. Even lower temperatures on the order of 50° to 90° C. are preferred to minimize urea loss.

Complete conversion can be obtained in relatively short contact times, particularly under acidic conditions. Also, as pointed out above, hydrolysis rate accelerates as temperature is increased. Thus hydrolysis periods of about 1 minute to about 1 hour are sufficient, although periods of about 5 minutes to about 30 minutes are generally the case. Obviously, shorter contact times will achieve the desired conversion at higher rates occasioned by higher reaction temperatures and lower pH levels. All of these variables should be correlated to obtain the desired degree of hydrolysis while minimizing byproduct formation, product destruction and urea loss by hydrolysis.

Following this procedure the aqueous phase will contain essentially all of the urea and minor amounts of cyanuric acid. Under the described conditions, cyanuric acid is soluble in water in concentrations of about 1 weight percent. Thus, the principle amount remains undissolved and can be separated by filtration, decanting, etc. The cyanuric acid can be recovered by precipitation upon cooling to a sufficiently low temperature to precipitate cyanuric acid, e.g., 10° C. or less. Urea will remain in the solution and can be reused by recycling to a manufacturing facility or by dehydration as described above. The effort required to recover and/or reuse dissolved urea depends on solution concentration. For that reason the amount of water used for hydrolysis should be only that required to hydrolyze and dissolve all of the urea formed in this step. For instance, urea is soluble in water in amounts of about 70 weight percent at 60° C. and about 40 weight percent at 0° C. Cyanuric acid concentration at 60° C. is less than 1 percent. Thus, urea hydrolysis at 60° C. with 2.5 weight parts water per weight part resultant urea (about 0.67 weight part water per weight part urea cyanurate) followed by cooling to 0° C. will leave essentially all of the urea and less than 1 weight percent cyanuric acid in solution at the lowest temperature. Under these conditions, liquid-solids separation gives 99 percent cyanuric acid recovery and leaves a concentrated urea solution (about 40 weight percent) for recycle, drying, etc.

Cyanuric acid has found utility in a number of applications including the manufacture of chlorinated isocyanurates used in bleaches, cleaning compounds and swimming pool sanitizers. These applications alone accounted for the consumption of twenty-six million pounds of chlorinated isocyanurates in 1966. Urea cyanurate has utility as an intermediate for the formation of cyanuric acid and thus for manufacturing the products mentioned above. It also has direct utility as a slow release nitrogen fertilizer. However, it should be applied directly to the soil. Foliar application is not preferred with most plants due to phytotoxicity.

EXAMPLE 1

Urea (435 grams) and sulfur (200 grams flowers of sulfur were added to a two-liter, three-neck flask provided with a 260° C. thermometer, a mechanical stirrer and water-cooled condenser. The stirrer was operated continuously. The materials were gradually heated to a temperature of 190° C. over a period of 20 minutes. Both the urea and sulfur were molten at this temperature. The sulfur, being less dense, formed a separate phase, a substantial part of which floated on top of the molten urea. The temperature was then gradually increased to 200° C. and held at that level for 10 minutes. At 195° C. the urea phase turned from its previous clear appearance to an opaque, milky color below the overlying sulfur layer and a white solid precipitate was evident.

The mixture was allowed to cool gradually to 80° C. and was mixed with 475 milliliters of water to form a dispersion of sulfur and a white, insoluble flocculent material. The sulfur and insoluble product were separated from the aqueous phase by filtration, washed with distilled water and decanted to separate a supernatant suspension of the white floc from the more dense sulfur particles. The susension was then filtered to recover 190 grams of the white insoluble material which was washed one with 500 milliliters acetone, twice with 200 milliliters carbon bisulfide and once more with 200 milliliters acetone, with filtering after each washing step.

Thin layer chromatography established that the recovered material was a single compound. This material decomposed without melting at a temperature of about 350° C. and was hydrolyzed in warm (60° C.) dilute sulfuric acid (1 percent) to urea and cyanuric acid. The insoluble product (preceeding hydrolysis) was identified as urea cyanurate by elemental analysis and infrared and mass spectroscopy.

EXAMPLE 2

Approximately 73 grams of cyanuric acid can be recovered from 100 grams of the urea cyanurate produced in Example 1 by hydrolysis in 70 grams of 1 weight percent $H_2SO_4$ at 60° C. for 30 minutes followed by cooling to 0° C. The undissolved cyanuric acid can be recovered by liquid-solids separation leaving a relatively concentrated urea solution (about 40 weight percent). The separated cyanuric acid can be further purified by water washing to remove trace urea.

I CLAIM:
1. The method of producing urea cyanurate from urea including the steps of heating undissolved urea with a catalytic amount of elemental sulfur under substantially anhydrous conditions to a temperature of about 190° to about 320° C. for a period sufficient to convert said urea to a reaction product containing urea cyanurate.

2. The method of claim 1 wherein said urea is heated to a temperature between about 190° and 260° C. for a period of at least about 1 minute in the presence of at least about 1 weight part elemental sulfur per 100 parts of said urea and in the presence of less than about 5 weight parts water per 100 weight parts urea.

3. The method of claim 1 wherein said reaction product is cooled to a temperature of about 110° C. or less before contacting with additional water.

4. The method of claim 1 wherein said reaction product is cooled to a temperature of about 110° C. or less, the thus-cooled reaction product is mixed with at least 10 weight parts water per 100 weight parts of said reaction product sufficient to form a liquid phase and a solid phase, and said solid phase is recovered from said liquid phase as said urea cyanurate.

5. The method of claim 4 wherein said recovered solid phase is washed with a solvent in which elemental sulfur is at least 5 times more soluble than is urea cyanurate to reduce the sulfur content of said urea cyanurate.

6. The method of claim 1 further comprising the steps of contacting said reaction product with at least about 1 mole of water per mole of urea cyanurate under conditions including a temperature of at least about 50° C., sufficient to hydrolyze said urea cyanurate to cyanuric acid.

7. The method of claim 6 wherein said hydrolysis is conducted at a temperature between about 50° and about 150° C. for a period of about 1 minute to about 1 hour in the presence of a mineral acid in an amount sufficient to produce a pH of about 6 or less, which hydrolysis conditions are correlated to hydrolyze said urea cyanurate to urea and cyanuric acid.

8. The method of claim 6 wherein the aqueous phase containing urea and the solid phase containing cyanuric acid resulting from hydrolysis of said urea cyanurate are separated to recover cyanuric acid as said solid phase.

* * * * *